(12) United States Patent
Bogie et al.

(10) Patent No.: US 11,395,918 B2
(45) Date of Patent: Jul. 26, 2022

(54) DEVICES, AND SYSTEMS FOR REMOTELY MONITORING AND TREATING WOUNDS OR WOUND INFECTIONS

(71) Applicants: The United States Government as Represented by the Department of Veterans Affairs, Washington, DC (US); Case Western Reserve University, Cleveland, OH (US)

(72) Inventors: Kath M. Bogie, Shaker Heights, OH (US); Christian A. Zorman, Euclid, OH (US)

(73) Assignees: United States Government as Represented by the Department of Veterans Affairs, Washington, DC (US); Case Western Reserve University, Cleveland, OH (US)

( * ) Notice: Subject to any disclaimer, the term of this patent is extended or adjusted under 35 U.S.C. 154(b) by 333 days.

(21) Appl. No.: 16/549,743

(22) Filed: Aug. 23, 2019

(65) Prior Publication Data
US 2020/0061379 A1 Feb. 27, 2020

Related U.S. Application Data

(60) Provisional application No. 62/722,471, filed on Aug. 24, 2018.

(51) Int. Cl.
*A61N 1/36* (2006.01)
*H05K 1/18* (2006.01)
(Continued)

(52) U.S. Cl.
CPC ............ *A61N 1/36031* (2017.08); *A61B 5/01* (2013.01); *A61F 13/0206* (2013.01);
(Continued)

(58) Field of Classification Search
CPC ........ A61N 1/0468; A61F 2013/00853; A61B 2562/0271; A61B 2562/043
See application file for complete search history.

(56) References Cited

U.S. PATENT DOCUMENTS 3,425,412 A * 2/1969 Pope .................. A61F 13/0203
D24/189
6,963,772 B2 * 11/2005 Bloom ..................... A61B 5/01
600/549
(Continued)

FOREIGN PATENT DOCUMENTS

WO WO-2017/195038 A1 11/2017
WO WO-2017195038 A1 * 11/2017 ............. A61B 5/445
(Continued)

OTHER PUBLICATIONS

Husain Al Hashimi, Omar Chaalal, Flexible temperature sensor fabrication using photolithography technique, Thermal Science and Engineering Progress, vol. 22, 2021, 100857, ISSN 2451-9049, https://doi.org/10.1016/j.tsep.2021.100857. (Year: 2021).*
(Continued)

*Primary Examiner* — Hoa C Nguyen
*Assistant Examiner* — John B Freal
(74) *Attorney, Agent, or Firm* — Ballard Spahr LLP (57) ABSTRACT

Devices and methods for remotely monitoring and treating wounds or wound infections are disclosed. A device can include a multi-layered, flexible substrate having a dressing layer positioned on a wound side of the substrate, and a flexible printed circuit board layer positioned on an electronics side of the substrate that is opposite the wound side of the dressing layer. A plurality of electrodes can be electrically coupled to the flexible printed circuit board. A plurality of temperature sensors can be electrically coupled
(Continued)

to the flexible printed circuit board. Systems including the described devices are also disclosed.

19 Claims, 4 Drawing Sheets

(51) Int. Cl.
    *H05K 1/11*     (2006.01)
    *A61F 13/02*     (2006.01)
    *A61N 1/04*     (2006.01)
    *A61B 5/01*     (2006.01)

(52) U.S. Cl.
    CPC ........ *A61F 13/0253* (2013.01); *A61N 1/0468* (2013.01); *A61N 1/0492* (2013.01); *H05K 1/115* (2013.01); *H05K 1/118* (2013.01); *H05K 1/189* (2013.01); *H05K 2201/0141* (2013.01); *H05K 2201/10151* (2013.01)

(56) References Cited

U.S. PATENT DOCUMENTS

| | | | |
|---|---|---|---|
| 7,687,678 B2* | 3/2010 | Jacobs | ................ A61K 9/0097 602/41 |
| 2010/0174343 A1 | 7/2010 | Andino et al. | |
| 2015/0289775 A1* | 10/2015 | Chon | ...................... B29C 39/10 264/102 |
| 2016/0287868 A1* | 10/2016 | Bogie | .................. A61N 1/0468 |
| 2016/0302674 A1* | 10/2016 | Moyer | ............... A61B 5/14552 |

FOREIGN PATENT DOCUMENTS

| | | | |
|---|---|---|---|
| WO | WO-2018/115461 A1 | 6/2018 | |
| WO | WO-2018115461 A1 * | 6/2018 | ............. A61B 5/145 |

OTHER PUBLICATIONS

Omega Sensors RTD Temperature vs. Resistance Table (Year: 2021).*
Omega RTD Sensors (Year: 2021).*
"Resistance thermometer", Wikipedia, Jul. 10, 2018 (Jul. 10, 2018), p. 1-2, [retrieved Feb. 11, 2020] via <https://en.wikipedia.org/w/index.php?title=Resistance_thermometer&oldid=849720779.
International Search Report and Written Opinion were dated Nov. 14, 2019 by the International Searching Authority for International Application No. PCT/US2019/047864, filed on Aug. 23, 2019 (Applicant—United States Government as represented by the Department of Veterans Affairs) (12 Pages).

* cited by examiner

DEVICES, AND SYSTEMS FOR REMOTELY MONITORING AND TREATING WOUNDS OR WOUND INFECTIONS

CROSS-REFERENCE TO RELATED APPLICATION

This application claims priority to and the benefit of the filing date of U.S. Provisional Patent Application No. 62/722,471, filed Aug. 24, 2018, which is incorporated herein by reference in its entirety.

FIELD

This application relates generally to devices, systems, and methods for remotely monitoring and/or treating wounds or wound infections. In exemplary configurations, such devices can comprise an integrated surface stimulation device (ISSD) as further disclosed herein.

SUMMARY

A device for treating wounds can comprise a multi-layered, flexible substrate having a dressing layer positioned on a wound side of the substrate. A flexible printed circuit board layer can be positioned on an electronics side of the substrate that is opposite the wound side of the dressing layer. A plurality of electrodes can be electrically coupled to the flexible printed circuit board. A plurality of temperature sensors can be electrically coupled to the flexible printed circuit board.

The dressing layer can defines a plurality of openings, wherein the plurality of electrodes are received within corresponding openings of the plurality of openings in the dressing layer, and wherein the plurality of temperature sensors are received within corresponding openings of the plurality of openings in the dressing layer.

A first temperature sensor of the plurality of temperature sensors can be configured for positioning within an area of a wound and a second temperature sensor can be spaced from the first temperature sensor by at least four centimeters along a longitudinal axis of the device.

The device can have a longitudinal axis. The plurality of electrodes can comprise a first electrode and a second electrode, wherein the first and second electrodes and the first and second temperature sensors are aligned along the longitudinal axis, wherein the first temperature sensor is positioned in a space between the first and second electrodes, and wherein the second temperature sensor is positioned outside of the space between the first and second electrodes.

The first temperature sensor can be spaced from the second temperature sensor by at least four centimeters.

The plurality of electrodes can be flexible doped PDMS electrodes.

At least a portion of the flexible printed circuit board layer can be transparent. The dressing layer can be at least partially transparent.

At least a portion of the flexible printed circuit board layer can further comprise an occlusive layer that surrounds the at least a portion of the flexible printed circuit board that is transparent.

The flexible printed circuit board layer can comprise an LCP layer comprising photolithographic patterning that defines copper traces.

The printed circuit board can further comprise laser machined via trenches that are electroplated with copper to define vias that extend between the copper traces and respective electrodes of the plurality of electrodes.

The plurality of electrodes can be photolithographically fabricated on the wound side of the printed circuit board.

The temperature sensors can comprise platinum and can be photolitographically fabricated on the wound side of the printed circuit board.

The plurality of temperature sensors can be configured to exhibit a linear response within a range between 35° C. and 40° C.

The device can further comprise a controller in electrical communication with the plurality of electrodes and the plurality of temperature sensors. The controller can be operative to: control an electrical current between at least two electrodes of the plurality of electrodes to provide a series of electrical stimulations to a wound and receive a signal from each temperature sensor of the plurality of temperature sensors.

The controller can be further operative to measure an impedance between the at least two electrodes of the plurality of electrodes during a time between electrical stimulations.

The controller can be further operative to transmit, to a remote module, a signal corresponding to the signal from each temperature sensor.

A system can comprise a device comprising a multi-layered, flexible substrate having a dressing layer positioned on a wound side of the substrate. A flexible printed circuit board layer can be positioned on an electronics side of the substrate that is opposite the wound side of the dressing layer. A plurality of electrodes can be electrically coupled to the flexible printed circuit board. A plurality of temperature sensors can be electrically coupled to the flexible printed circuit board. A controller can be in electrical communication with the plurality of electrodes and the plurality of temperature sensors, wherein the controller is operative to: control an electrical current between at least two electrodes of the plurality of electrodes to provide a series of electrical stimulations to a wound, and receive a signal from each temperature sensor of the plurality of temperature sensors. A remote module can be in communication with the controller of the device.

A method can comprise positioning a device on a patient, the device comprising a multi-layered, flexible substrate having a dressing layer positioned on a wound side of the substrate, and a flexible printed circuit board layer positioned on an electronics side of the substrate that is opposite the wound side of the dressing layer, a plurality of electrodes electrically coupled to the flexible printed circuit board, and a plurality of temperature sensors electrically coupled to the flexible printed circuit board. The device can be positioned on the patient so that a first temperature sensor of the first plurality of temperature sensors is positioned within an area of a wound and a second temperature sensor of the plurality of temperature sensors is positioned at a location spaced from the area of the wound.

The method can further comprise determining an infection status of the wound based on a temperature difference between the first temperature sensor and the second temperature sensor.

The device can be positioned on the patient so that the plurality of electrodes are positioned at respective locations spaced from the area of the wound.

A distance by which the second temperature sensor is spaced from the area of the wound can be greater than respective distances by which the plurality of electrodes are spaced from the area of the wound.

BRIEF DESCRIPTION OF THE DRAWINGS

These and other aspects of the invention will become more apparent in the detailed description in which reference is made to the appended drawings wherein.

DETAILED DESCRIPTION

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a temperature sensor" or "an adhesive" can include two or more such temperature sensors or adhesives unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Optionally, in some aspects, when values are approximated by use of the antecedent "about," "generally," or "substantially," it is contemplated that values within up to 15%, up to 10%, or up to 5% (above or below) of the particularly stated value or characteristic can be included within the scope of those aspects.

As used herein, the terms "optional" or "optionally" mean that the subsequently described event or circumstance may or may not occur, and that the description includes instances where said event or circumstance occurs and instances where it does not.

As used herein, the term "communicatively coupled" refers to a condition in which two components are capable of communicating with each other using any conventional wired or wireless communication protocol, including, without limitation, direct/cable connection, WiFi connection, Bluetooth® connection, and the like.

The word "or" as used herein means any one member of a particular list and also includes any combination of members of that list.

As used herein, the term "via" refers to a vertical interconnect access (VIA) structure or component as is known in the art.

As used in this application, the terms "the device" and "ISSD" are used interchangeably.

Described herein are devices, systems, and methods for remotely monitoring and/or treating a wound or wound infection. It is contemplated that the disclosed devices can be used in combination with various processing, monitoring, and/or treatment components to provide a system. Optionally, the disclosed device can be communicatively coupled to a remote computing device, such as a computer, a tablet, a smartphone, and the like. Optionally, such remote computing devices can include processing circuitry that is configured to execute application software that remotely controls and monitors operation of the device.

Construction of the Substrate

Figure 1A:
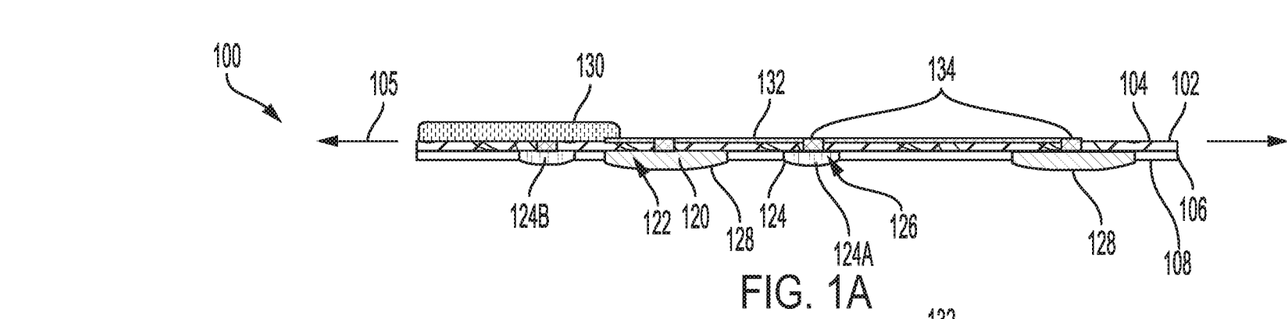
FIG. 1A is a cross-sectional view of an exemplary device having a bilayer substrate, stimulating electrodes and vias, with the wound bed lying between the electrodes.
Figure 1B:
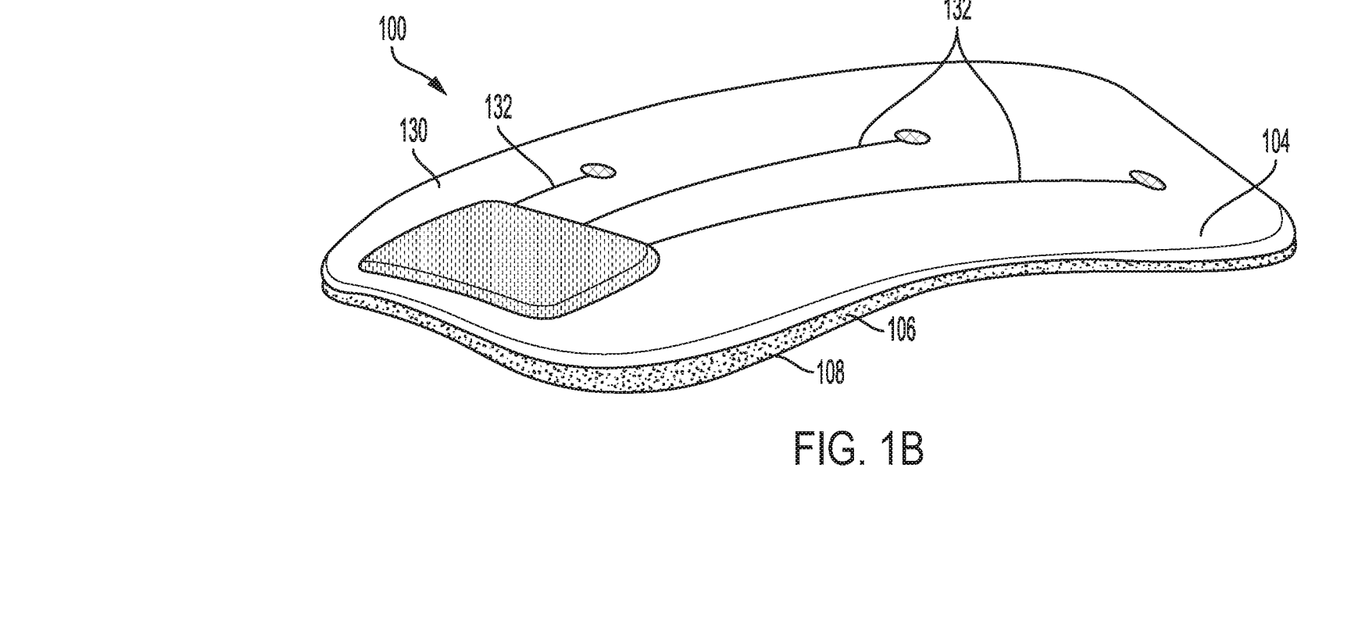
FIG. 1B is a top perspective view of the device of FIG. 1A, showing the power/control module, vias, and interconnects between the vias and power/control module.
Figure 2:
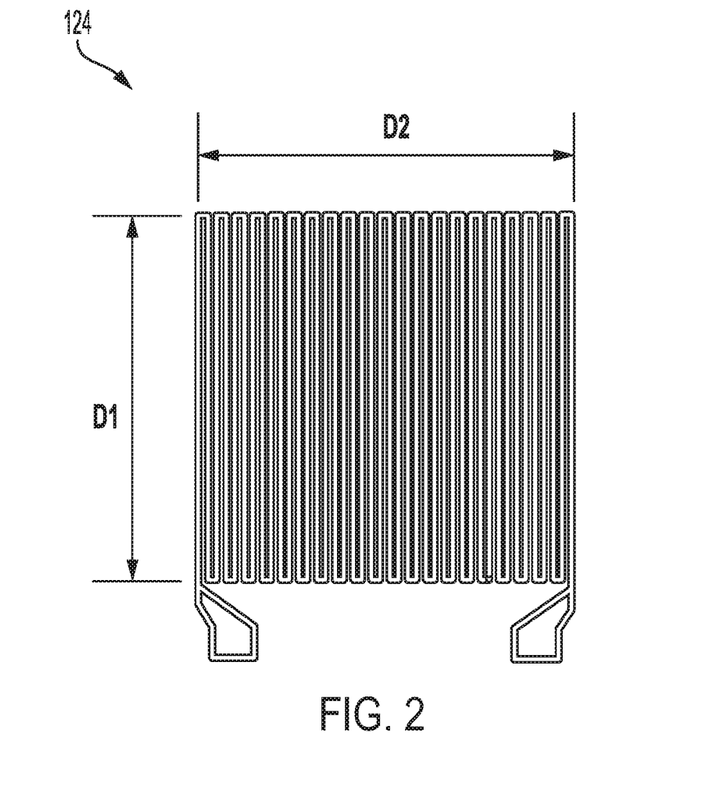
FIG. 2 is a schematic of a microfabricated TCR temperature sensor.
Figure 3:
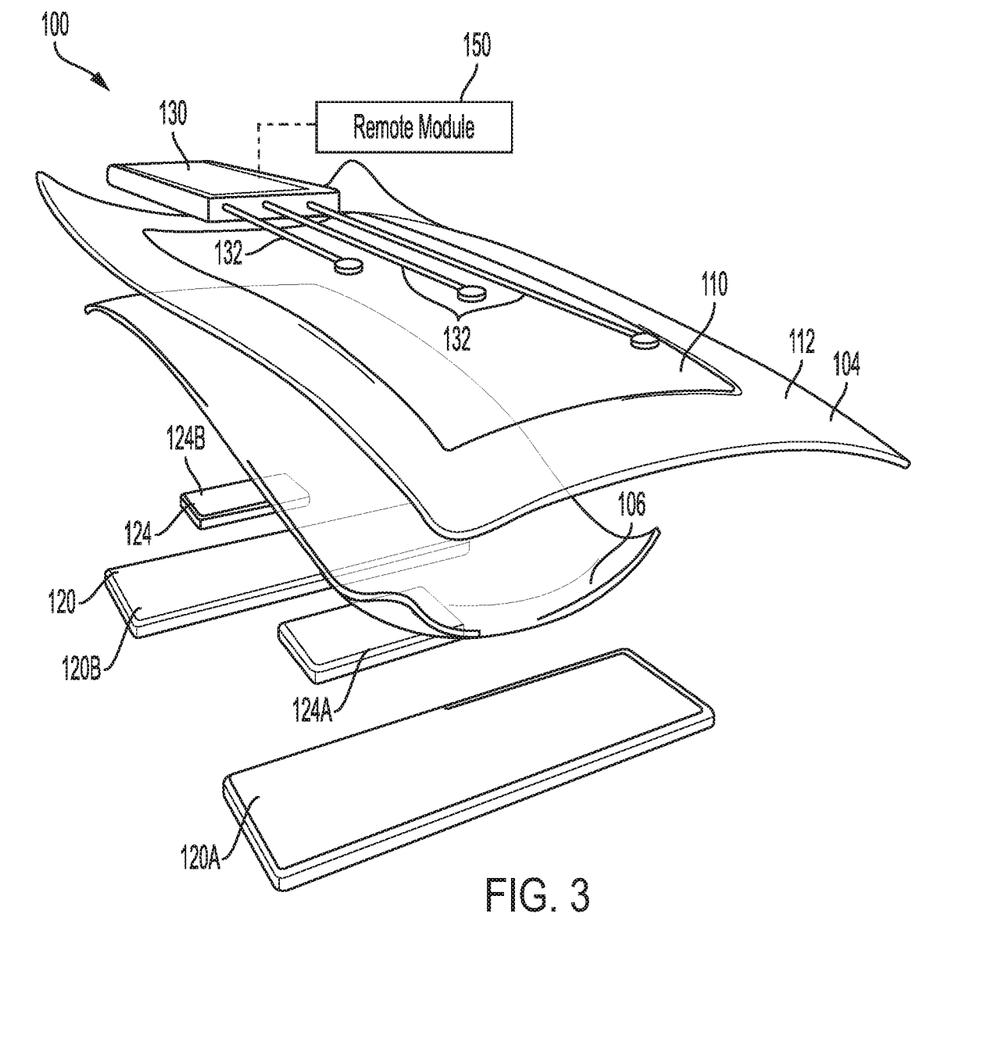
FIG. 3 is an exploded view of the device of FIG. 1A.

The wound treatment device can have a layered construction. The packaged stimulation/control module can be supported on the bandage substrate as shown in FIGS. 1A-2. In exemplary non-limiting aspects, the layers of the substrate can comprise: (1) a commercially available, commonly used wound dressing; (2) an absorbent material to manage wound exudate and support the stimulating electrodes and sensor; (3) the stimulating electrodes and sensors; and (4) adhesive hydrogel to ensure contact with the wound and periwound area. More specifically, and in further optional aspects, an absorbent material can be included as an intermediate layer in order to absorb wound exudate. A suitable absorbent material for this application can exhibit consistency in size and shape once soaked and not leak fluid once soaked. In further aspects, the electrodes can be constructed from conductive fabric. Optionally, in these aspects, it is contemplated that a suitable conductive fabric for this application can have low impedance, can maintain a stable voltage over the length of the electrode, will not heat when sustained current is applied, and can remain chemically stable when sterilized and when exposed to the wound environment. Examples of suitable conductive fabrics include SHIELDEX TECHNIK-TEX P130+B and SHIELDEX TECHNIK-TEX P130+B conductive fabrics sold by V Technical Textiles, Inc. of Palmyra, N.Y. In still further aspects, the electrodes can be attached to the power/control module using conductive thread, which can serve as a conductive via for vertical interconnects. Examples of a suitable conductive thread can include 235/43 DTEX HC+B conductive thread sold by V Technical Textiles, Inc. of Palmyra, N.Y. An appropriate adhesive can also be used to mechanically and electrically secure the electrodes. Optionally, the adhesive can be a conductive adhesive, such as a conductive epoxy adhesive. Suitable adhesives include MG Products 8331 silver conductive epoxy adhesive.

In some embodiments, the device 100 can comprise a substrate 102 having a top layer 104 and an absorbent layer 106. A medical grade pressure sensitive adhesive coating 108 can be disposed on the lower face of the substrate layer for adhering the device 100 to the patient. The top layer 104 can optionally comprise a flexible, transparent window 110 and a flexible occlusive layer 112 that extends around the circumference of the transparent window 110. The transparent window 110 can optionally comprise a flexible biocompatible polymeric material, such as SYLGARD polymer (manufactured by DOW). The flexible occlusive layer 112 can serve to seal against the skin and prevent wound exudate from escaping. Optionally, the occlusive layer and the transparent window can be provided as a single, integral structure. The absorbent layer 106 can optionally be transparent or partially transparent to provide, in cooperation with the transparent window 110 of the top layer 104, visibility of the wound.

A plurality of electrodes 120 (optionally, a first electrode 120A and a second electrode 120B) can be disposed on an underside of the substrate 102. Optionally, the absorbent layer 106 can define holes 122 therethrough, and the electrodes 120 can be positioned within the holes 122 and attached to the underside of the top layer 104. In further embodiments, the electrodes 120 can attach to the underside of the absorbent layer 106. In use, it is contemplated that the electrodes 120 can be configured to provide electrical stimulation as further disclosed herein.

A plurality of temperature sensors 124 (optionally, a first temperature sensor 124A and a second temperature sensor 124B) can be disposed on an underside (wound side) of the substrate 102. Optionally, the absorbent layer 106 can define holes 126 therethrough, and the temperature sensors 124 can be positioned within the holes 126 and attached to the underside of the top layer 104. In further embodiments, the temperature sensors 124 can attach to the underside of the absorbent layer 106.

The electrodes 120 can be periwound electrodes. That is, in use, the electrodes 120 can be positioned on the skin surrounding the wound and, thus, be spaced (e.g., slightly spaced) from the wound bed (i.e., the area of the wound). The first temperature sensor 124A can be positioned between the electrodes 120, and the second temperature sensor 124B can be positioned outside of the electrodes 120. Thus, the first temperature sensor 124A can be positioned over or within the wound bed, while the second temperature sensor can be positioned away from (i.e., depending on the orientation of the wound and the device, laterally or vertically spaced from) the wound bed. For example, when the wound bed is oriented horizontally, it is contemplated that the second temperature sensor can be sufficiently horizontally spaced from the wound bed so that the temperature measured by the second temperature sensor reflects ambient/systemic temperature information (rather than the temperature at or within the wound). As shown in FIG. 1A, the device 100 can have a longitudinal axis 105. Optionally, the first and second temperature sensors 124A, 124B and the first and second electrodes 120A, 120B can be aligned along the longitudinal axis 105. In some embodiments, along the longitudinal axis 105, the first temperature sensor 124A can be disposed between the first and second electrodes 120A, 120B, and the second temperature sensor 124B can be disposed outside of the space between the first and second electrodes 120A, 120B. Thus, when the electrodes are positioned on opposite sides of the wound bed, the first temperature sensor 124A can be positioned in the wound bed, and the second temperature sensor 124B can be positioned outside the wound bed (on the opposite side of the second electrode 120B from the first temperature sensor 124A). In some embodiments, the first and second temperature sensors 124A, 124B can be spaced from each other by about two centimeters, about three centimeters, about four centimeters, about five centimeters, about six centimeters, about seven centimeters, about eight centimeters, about nine centimeters, about ten centimeters, about twelve centimeters, or more. In some embodiments, the first and second electrodes 120A, 120B can be spaced from each other by about two centimeters, about three centimeters, about four centimeters, about five centimeters, about six centimeters, about seven centimeters, about eight centimeters, about nine centimeters, about ten centimeters, about twelve centimeters, about fifteen centimeters, about twenty centimeters, or about twenty-five centimeters or more. Optionally, it is contemplated that the spacing between the first and second electrodes 120A, 120B can be greater than the spacing between the first and second temperature sensors 124A, 124B. Alternatively, it is contemplated that the spacing between the first and second electrodes 120A, 120B can be equal or substantially equal to the spacing between the first and second temperature sensors 124A, 124B. In still a further alternative, it is contemplated that the spacing between the first and second electrodes 120A, 120B can be less than the spacing between the first and second temperature sensors 124A, 124B.

A layer of hydrogel 128 can cover the lower surfaces of the electrodes 120 and/or the temperature sensors 124. Optionally, the hydrogel 128 can be a conductive hydrogel as is known in the art. Examples of hydrogels that can be used are disclosed in Staples, N. A., Goding, J. A., Gilmour, A. D., Aristovich, K. Y., Byrnes-Preston, P., Holder, D. S., . . . & Green, R. A. (2018). Conductive hydrogel electrodes for delivery of long-term high frequency pulses. Frontiers in neuroscience, 11, 748. The foregoing article is hereby incorporated by reference herein in its entirety.

A control module 130 can provide power to the electrodes 120 and the temperature sensors 124. The control module 130 can electrically couple to the electrodes 120 and the temperature sensors 124 by conductors 132 that extend from the control module 130, along the substrate 120. The conductors can extend through via trenches to define vias 134. Optionally, the conductors 132 can comprise conductive traces (e.g., copper traces). However, it is contemplated that any conventional conductive material can be used. The control module 130 can include a power source, such as a battery. Alternatively, it is contemplated that the control module 130 can be electrically coupled to an external power source (for example, using a cord or cable).

In one aspect, fabrication of the mechanically flexible substrate of the device can comprise a copper (Cu)-clad flex-electronics liquid crystal polymer (LCP) sheet. Photolithographic patterning can be used to fabricate Cu contact pads for the stimulation electrodes on the wound (bottom) side of the substrate and interconnect traces for the electrodes and temperature sensors on the electronics (top) side. The temperature sensors 124 can be platinum temperature sensors and can be photolithographically fabricated on the wound side of the substrate. Via trenches for vertical interconnects 134 between the two sides of the substrate can be defined by laser micromachining and can be filled by Cu electroplating to define the vias 134. The electrodes 120 can optionally be multi-layered, multi-material electrodes. The electrodes 120 can comprise an electrically-conductive adhesive strip for connection to the conductors 132. The layer of hydrogel 128 can provide a direct stimulation interface and can be laser micro-machined and attached to the contact pads on the wound-side of the substrate. In further embodiments, the electrodes can comprise doped polydimethylsiloxane (PDMS). Such electrodes can be flexible to conform to the shape of the portion of a patient's body where the device is applied.

In exemplary non-limiting aspects, doped, conductive PDMS electrodes can be made by mixing carbon-black with PDMS (CB-PDMS) using the following procedure. Carbon black of the proper particle size can be prepared by gently grinding carbon granules in a ceramic mortar and sieving the resulting powder to 0.1 mm. Next, the appropriate amount of filtered powder to achieve the desired carbon-black concentration in the PDMS composite can dispensed into a clean beaker or other suitable container. Next, toluene (e.g., 10 mL) can be added to the carbon black and the beaker can then be sonicated for 30 min (e.g., using a QSONICA Q500 probe, 500 W, 20 kHz, 30% duty cycle) to ensure thorough mixing. Next, Part A of ECOFLEX 00-10 elastomer can be added to the beaker, followed by a 10 min sonication. Then, Part B of ECOFLEX 00-10 elastomer can be added to the beaker, followed by a 10 min sonication. (ECOFLEX 00-10 is a two-part PDMS elastomer and can be desirable in the CB-PDMS layer because of its high elasticity and low hardness relative to other forms of PDMS. This can be important because the addition of carbon-black can have an effect of reducing the elasticity of the composite structure.) The CB-PDMS-toluene mixture can subsequently be poured into a tray (e.g., an aluminum tray) and magnetically stirred at room temperature to facilitate the evaporation of the toluene. Once the mixture becomes too viscous to stir, it can be transferred to a vacuum desiccator and exposed to a vacuum environment until the composite reached a toluene concentration below 3 wt %. At this point, the mixture/composite can be cast into its final dimensions (e.g., in a stencil), fully cured at room temperature, and completely degassed.

In clinical applications, it is contemplated that a wound dressing can be modified to properly receive the flexible substrate by cutting access windows for the hydrogel electrodes. A commercial adhesive can mechanically join the dressing and flexible substrate. Assembly can be completed by mounting the packaged electronics to the electronics side of the flexible substrate using adhesive bonding and electrically linking the two (i.e., the packaged electronics and the electronics side of the flexible substrate) using standard flex-electronic connectors. At this point, the disposable ICCD (device) substrate can be ready for sterilization.

Temperature Sensing

The optimal wound bed temperature for healing can be 33° C. However, wound bed temperature can fluctuate greatly due to infection, ischemia or even simply due to dressing changes. Thus, biocompatible temperature sensors of appropriate range and sensitivity can be utilized. Temperature Coefficient of Resistance (TCR) is a material properties parameter used to relate the change in resistance with change of temperature. In exemplary aspects, the temperature sensors disclosed herein can measure a change in resistance that can be converted to a corresponding temperature change using conventional methods (for example, using TCR parameters).

In use, at least one temperature sensor can be located over the wound bed (i.e., the area of the wound), and at least one other temperature sensor can be located over intact periwound skin. The temperature sensor located over the periwound skin (i.e., spaced away from the wound area) can provide ambient/systemic temperature that can provide insight to the local wound microenvironment. The temperature sensors can be intentionally made with minimum sufficient surface area in contact with the wound or skin of the patient so as to minimize their impact on the electrical stimulation (ES) performance of the device. In exemplary aspects, it is contemplated that the actual "contact" surface area between each temperature sensor and the patient can be range from about one square millimeter to about 200 square millimeters, from about 1.25 square millimeters to about 150 square millimeters, from about 1.5 square millimeters to about 100 square millimeters, from about 1.75 square millimeters to about 25 square millimeters, or from about two square millimeters to about five square millimeters. Thermal noise can be corrected by subtracting the periwound temperature measurement from the measurement from the sensor located over the wound bed. A temperature sensor can be created by inkjet printing conductive traces on a robust substrate or by other appropriate means of microfabrication. The substrate can be electrically insulating, chemically stable and biocompatible. Some optional materials for the substrate can include liquid crystal polymer, polyimide, parylene, polyethylene terephthalate (PET), polyethylene naphthalate (PEN). A schematic of an exemplary sensor can be seen in FIG. 2. The temperature sensor can have a rectangular or generally rectangular profile, having a length dimension D1 and a width dimension D2. Optionally, the length dimension D1 can be equal to the width dimension D2. Optionally, the length dimension D1 can be about sixteen millimeters, and the width dimension D2 can be about sixteen millimeters. However, it is contemplated that other suitable dimensions can be used. Optionally, both the traces and the spacing in between the traces are 0.2 mm thick. However, other spacing and trace thicknesses can be used. For example, as disclosed herein, it is contemplated that the traces can be structured to minimize the total area of contact between the traces and the patient. Thus, the actual contact area between the sensors and the patient (excluding void spaces corresponding to the spacing between the traces) can be significantly less than the total area covered by the sensors (as reflected by the total length dimension D1 and the total width dimension D2). Contact pads on the sensor electrodes can be connected to the power/control module by conducting vias, which can comprise holes or openings that extend through at least a portion of the thickness of the device as further disclosed herein. In use, the sensor can exhibit a linear response within the clinically relevant range of about 35° C. to about 40° C. (about 95° F. to about 104° F.). For example, the resistance across the temperature sensor can increase linearly with temperature increase within said range.

Impedance Sensing

It is contemplated that changes in wound impedance (i.e., the impedance across the wound) over time can be an indicator of progress of wound closure and healing. For example, an open wound can have an impedance of 1-5Ω, whereas healed human skin can have an impedance of at least an order of magnitude higher and, in some situations, about 10 kΩ. The impedance difference can be primarily due to the stratum corneum. As the wound heals, area impedance of the wound can increase, and an up-turn can occur as re-epithelialization occurs. Moreover, excess moisture in the wound bed due to exudate can substantially lower the impedance across the wound. Thus, measurement of the wound impedance can enable monitoring of both progress of the wound as well as excess moisture accumulation. The impedance between the electrodes can be measured in intervals between deliveries of therapeutic ES. In this way, a clinician can remotely monitor the status of the wound in real time without disturbing the wound environment.

Control Module

The control module 130 can control the current and/or voltage to the electrodes 120 for providing electrical stimulation. Further, the control module 130 can measure impedance between electrodes using conventional methods. Optionally, it is contemplated that the control module 130 can comprise or be in communication with an impedance meter as is known in the art. In use, the impedance meter, through the control module 130, can apply an AC voltage source across the wound. The impedance meter can receive signals from the electrodes that are indicative of the voltage across and the current through the wound. Using conventional techniques, the impedance meter can then determine the magnitude of the impedance based upon the ratio between the measured voltage and the measured current. In some embodiments, the control module 130 can comprise a display for displaying various information, including temperature measurements and impedance measurements.

In some embodiments, the control module 130 can be communicatively coupled (i.e., communicate using wired or wireless connection) to a remote module 150. In some embodiments, the remote module 150 can be a remote monitor. In further embodiments, the remote module 150 can perform certain control and/or processing functions. For example, the control module 130 can receive signals from the temperature sensors 124 (e.g., signals indicative of resistance measurements by the sensors as further disclosed herein). In some embodiments, the control module 130 can process said signals for conversion to a temperature measurement (e.g., using TCR parameters). In these embodiments, it is contemplated that the control module can comprise at least one processor and a memory that stores instructions that, when executed by the at least one processor, determine the temperature measurement based on the received signals. In further embodiments, the remote module 150 can receive and process said signals for conversion to a temperature measurement. Similarly, the remote module 150 can display various information, including temperature measurements and impedance measurements. Further, the remote module 150 can provide an interface through which a clinician can control the device 100 (e.g., begin or end the ES as well as change the properties of the ES).

Optionally, in exemplary aspects, the remote module 150 can be provided as a remote computing device, such as, for example and without limitation, a smartphone, a tablet, a laptop computer, or a desktop computer. In these aspects, it is further contemplated that the remote module 150 can comprise at least one processor and a memory in communication with the processor. The memory can store structures that, when executed by the processor, determine information concerning the wound of the patient, including the temperature measurement, impedance measurements, change in temperature, and change in impedance.

In exemplary aspects, it is contemplated that the control module 130 and the remote module 150 (when provided) can comprise respective user interfaces (e.g., keyboards, touchscreens, dials, and the like) that allow for direct communication between a clinician and the control module and remote module. In use, it is contemplated that the control module 130 and/or the remote module 150 can be configured to control and adjust the duration, intensity/voltage, and/or frequency of the electrical stimulation that is delivered through the electrodes as disclosed herein.

Kit

A kit can comprise a plurality of devices 100. The devices in the kit can be of varying sizes. Each device 100 of the kit can be configured for a respective (optionally, different) size or shape of wound. Thus, it is contemplated that each device 100 of the kit can differ in at least one (optionally, a plurality) of the following parameters from at least one other device (optionally, each other device) of the kit: spacing between electrodes; spacing between temperature sensors; length or width of the absorbent layer 106; electrical stimulation parameters; length or width of the temperature sensors; or length or width of the electrodes. For example, a first device in the kit can be configured to treat a two inch by two inch wound. The absorbent layer 106 can therefore be substantially larger than two inches by two inches. The first and second electrodes 120A, 120B can be spaced greater than two inches, with the first temperature sensor being positioned between the two electrodes and the second electrode being positioned between the first and second temperature sensors (so that the second temperature sensor will be outside the wound area). A second device can be configured to treat a three inch by four inch wound. The absorbent layer 106 can therefore be substantially larger than three inches by four inches. The first and second electrodes 120A, 120B can be spaced greater than three inches.

Computing Device

Figure 4:
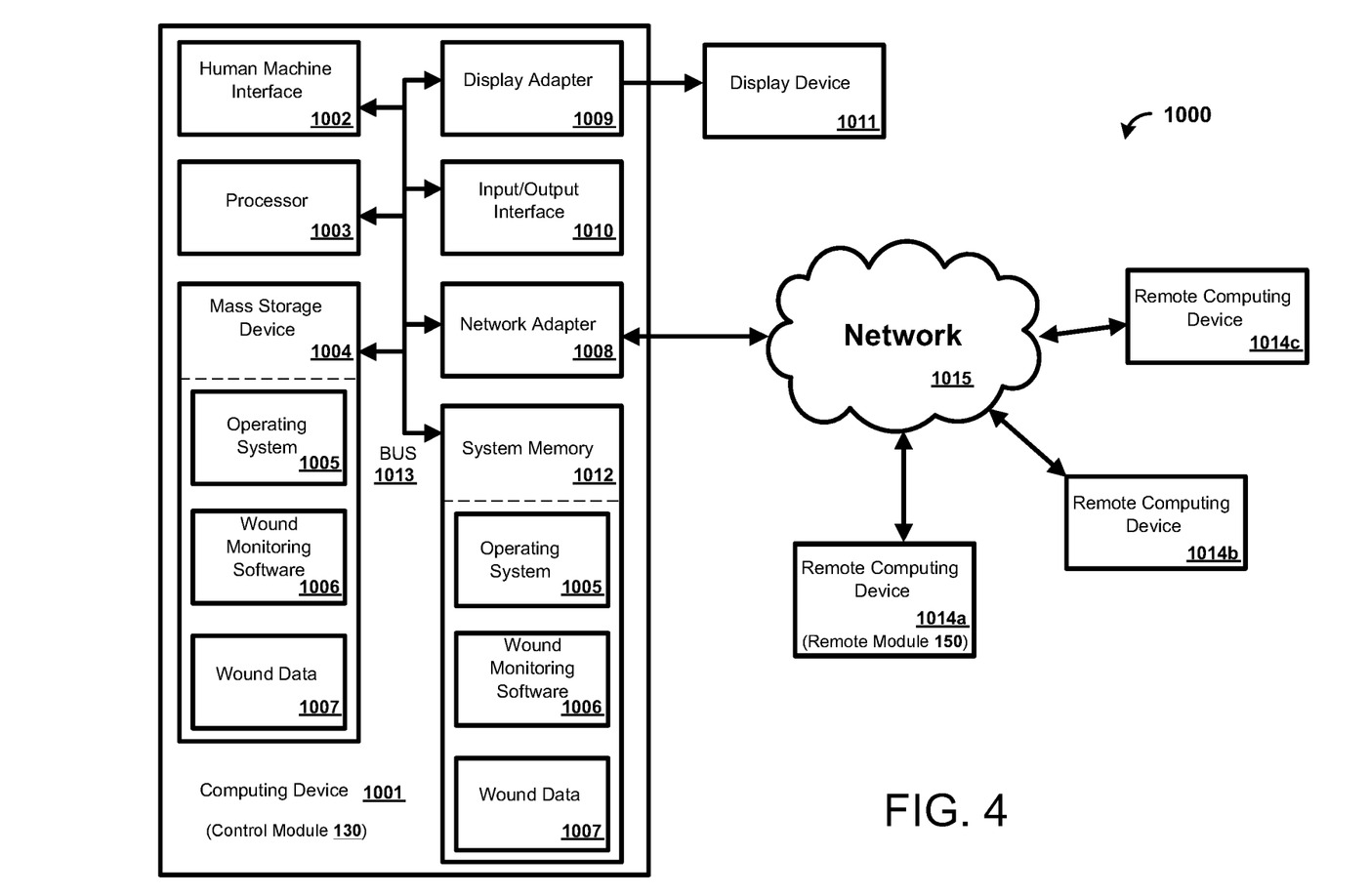
FIG. 4 schematically depicts a computing device that is operable to perform various aspects of the methods disclosed herein.

FIG. 4 shows a system 1000 including an exemplary configuration of a control module 130 for use with the device 100. As shown, the control module 130 can be provided as a computing device 1001, while the remote module 150 (when provided) can be provided as a remote computing device. For example, the computing device 1001 can perform various aspects of monitoring the temperature and impedance readings from the device 100. Moreover, the computing device 1001 can control some or all aspects of ES treatment.

The computing device 1001 may comprise one or more processors 1003, a system memory 1012, and a bus 1013 that couples various components of the computing device 1001 including the one or more processors 1003 to the system memory 1012. In the case of multiple processors 1003, the computing device 1001 may utilize parallel computing.

The bus 1013 may comprise one or more of several possible types of bus structures, such as a memory bus, memory controller, a peripheral bus, an accelerated graphics port, and a processor or local bus using any of a variety of bus architectures.

The computing device 1001 may operate on and/or comprise a variety of computer readable media (e.g., non-transitory). Computer readable media may be any available media that is accessible by the computing device 1001 and comprises, non-transitory, volatile and/or non-volatile media, removable and non-removable media. The system memory 1012 has computer readable media in the form of volatile memory, such as random access memory (RAM), and/or non-volatile memory, such as read only memory (ROM). The system memory 1012 may store data such as wound data 1007 and/or program modules such as operating system 1005 and wound monitoring software 1006 that are accessible to and/or are operated on by the one or more processors 1003.

The computing device 1001 may also comprise other removable/non-removable, volatile/non-volatile computer storage media. The mass storage device 1004 may provide non-volatile storage of computer code, computer readable instructions, data structures, program modules, and other data for the computing device 1001. The mass storage device 1004 may be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules may be stored on the mass storage device 1004. An operating system 1005 and wound monitoring software 1006 may be stored on the mass storage device 1004. One or more of the operating system 1005 and wound monitoring software 1006 (or some combination thereof) may comprise program modules and the wound monitoring software 1006. Wound data 1007 may also be stored on the mass storage device 1004. Wound data 1007 may be stored in any of one or more databases known in the art. The databases may be centralized or distributed across multiple locations within the network 1015.

A user (e.g., the clinician) may enter commands and information into the computing device 1001 using an input device (not shown). Such input devices comprise, but are not limited to, a keyboard, pointing device (e.g., a computer mouse, remote control), a microphone, a joystick, a scanner, tactile input devices such as gloves, and other body coverings, motion sensor, and the like. These and other input devices may be connected to the one or more processors 1003 using a human machine interface 1002 that is coupled to the bus 1013, but may be connected by other interface and bus structures, such as a parallel port, game port, an IEEE 1394 Port (also known as a Firewire port), a serial port, network adapter 1008, and/or a universal serial bus (USB).

A display device 1011 may also be connected to the bus 1013 using an interface, such as a display adapter 1009. It is contemplated that the computing device 1001 may have more than one display adapter 1009 and the computing device 1001 may have more than one display device 1011. A display device 1011 may be a monitor, an LCD (Liquid Crystal Display), light emitting diode (LED) display, television, smart lens, smart glass, and/or a projector. In addition to the display device 1011, other output peripheral devices may comprise components such as speakers (not shown) and a printer (not shown) which may be connected to the computing device 1001 using Input/Output Interface 1010. Any step and/or result of the methods may be output (or caused to be output) in any form to an output device. Such output may be any form of visual representation, including, but not limited to, textual, graphical, animation, audio, tactile, and the like. The display 1011 and computing device 1001 may be part of one device, or separate devices.

The computing device 1001 may operate in a networked environment using logical connections to one or more remote computing devices 1014a,b,c. A remote computing device 1014a,b,c may be a personal computer, computing station (e.g., workstation), portable computer (e.g., laptop, mobile phone, tablet device), smart device (e.g., smartphone, smart watch, activity tracker, smart apparel, smart accessory), security and/or monitoring device, a server, a router, a network computer, a peer device, edge device or other common network node, and so on. Logical connections between the computing device 1001 and a remote computing device 1014a,b,c may be made using a network 1015, such as a local area network (LAN) and/or a general wide area network (WAN). Such network connections may be through a network adapter 1008. A network adapter 1008 may be implemented in both wired and wireless environments. Such networking environments are conventional and commonplace in dwellings, offices, enterprise-wide computer networks, intranets, and the Internet. It is contemplated that the remote computing devices 1014a,b,c can optionally have some or all of the components disclosed as being part of computing device 1001.

Application programs and other executable program components such as the operating system 1005 are shown herein as discrete blocks, although it is recognized that such programs and components may reside at various times in different storage components of the computing device 1001, and are executed by the one or more processors 1003 of the computing device 1001. An implementation of wound monitoring software 1006 may be stored on or sent across some form of computer readable media. Any of the disclosed methods may be performed by processor-executable instructions embodied on computer readable media.

Exemplary Aspects

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: A device comprising: a multi-layered, flexible substrate having a dressing layer positioned on a wound side of the substrate, and a flexible printed circuit board layer positioned on an electronics side of the substrate that is opposite the wound side of the dressing layer; a plurality of electrodes electrically coupled to the flexible printed circuit board; and a plurality of temperature sensors electrically coupled to the flexible printed circuit board.

Aspect 2: The device of aspect 1, wherein the dressing layer defines a plurality of openings, wherein the plurality of electrodes are received within corresponding openings of the plurality of openings in the dressing layer, and wherein the plurality of temperature sensors are received within corresponding openings of the plurality of openings in the dressing layer.

Aspect 3: The device of aspect 1 or aspect 2, wherein a first temperature sensor of the plurality of temperature sensors is configured for positioning within an area of a wound and a second temperature sensor is spaced from the first temperature sensor by at least four centimeters along a longitudinal axis of the device.

Aspect 4: The device of aspect 3, wherein the device has a longitudinal axis, wherein the plurality of electrodes comprises a first electrode and a second electrode, wherein the first and second electrodes and the first and second temperature sensors are aligned along the longitudinal axis, wherein the first temperature sensor is positioned in a space between the first and second electrodes, and wherein the second temperature sensor is positioned outside of the space between the first and second electrodes.

Aspect 5: The device of aspect 4, wherein the first temperature sensor is spaced from the second temperature sensor by at least four centimeters.

Aspect 6: The device of any one of the preceding aspects, wherein the plurality of electrodes are flexible doped PDMS electrodes.

Aspect 7: The device of any one of the preceding aspects, wherein at least a portion of the flexible printed circuit board layer is transparent, and wherein the dressing layer is at least partially transparent.

Aspect 8: The device of any one of the preceding aspects, wherein at least a portion of the flexible printed circuit board layer further comprises an occlusive layer that surrounds the at least a portion of the flexible printed circuit board that is transparent.

Aspect 9: The device of any one of the preceding aspects, wherein the flexible printed circuit board layer comprises an LCP layer comprising photolithographic patterning that defines copper traces.

Aspect 10: The device of any one of the preceding aspects, wherein the printed circuit board further comprises laser machined via trenches that are electroplated with copper to define vias that extend between the copper traces and respective electrodes of the plurality of electrodes.

Aspect 11: The device of any one of the preceding aspects, wherein the plurality of electrodes are photolithographically fabricated on the wound side of the printed circuit board.

Aspect 12: The device of any one of the preceding aspects, wherein the temperature sensors comprise platinum and are photolitographically fabricated on the wound side of the printed circuit board.

Aspect 13: The device of any one of the preceding aspects, wherein the plurality of temperature sensors are configured to exhibit a linear response within a range between 35° C. and 40° C.

Aspect 14: The device of any one of the preceding aspects, further comprising: a controller in electrical communication with the plurality of electrodes and the plurality of temperature sensors, wherein the controller is operative to: control an electrical current between at least two electrodes of the plurality of electrodes to provide a series of electrical stimulations to a wound, and receive a signal from each temperature sensor of the plurality of temperature sensors.

Aspect 15: The device of aspect 14, wherein the controller is further operative to measure an impedance between the at least two electrodes of the plurality of electrodes during a time between electrical stimulations.

Aspect 16: The device of aspect 14 or aspect 15, wherein the controller is further operative to transmit, to a remote module, a signal corresponding to the signal from each temperature sensor.

Aspect 17: A system comprising: a device comprising a multi-layered, flexible substrate having a dressing layer positioned on a wound side of the substrate, and a flexible printed circuit board layer positioned on an electronics side of the substrate that is opposite the wound side of the dressing layer, a plurality of electrodes electrically coupled to the flexible printed circuit board, a plurality of temperature sensors electrically coupled to the flexible printed circuit board, and a controller in electrical communication with the plurality of electrodes and the plurality of temperature sensors, wherein the controller is operative to: control an electrical current between at least two electrodes of the plurality of electrodes to provide a series of electrical stimulations to a wound, receive a signal from each temperature sensor of the plurality of temperature sensors; and a remote module in communication with the controller of the device.

Aspect 18: A method comprising: positioning a device on a patient, the device comprising a multi-layered, flexible substrate having a dressing layer positioned on a wound side of the substrate, and a flexible printed circuit board layer positioned on an electronics side of the substrate that is opposite the wound side of the dressing layer, a plurality of electrodes electrically coupled to the flexible printed circuit board, and a plurality of temperature sensors electrically coupled to the flexible printed circuit board, wherein the device is positioned on the patient so that a first temperature sensor of the first plurality of temperature sensors is positioned within an area of a wound and a second temperature sensor of the plurality of temperature sensors is positioned at a location spaced from the area of the wound.

Aspect 19: The method of aspect 18, further comprising: determining an infection status of the wound based on a temperature difference between the first temperature sensor and the second temperature sensor.

Aspect 20: The method of aspect 19, wherein the device is positioned on the patient so that the plurality of electrodes are positioned at respective locations spaced from the area of the wound.

Aspect 21: The method of aspect 20, wherein a distance by which the second temperature sensor is spaced from the area of the wound is greater than respective distances by which the plurality of electrodes are spaced from the area of the wound.

Aspect 22: A kit comprising: a plurality of devices comprising: a multi-layered, flexible substrate having a dressing layer positioned on a wound side of the substrate, and a flexible printed circuit board layer positioned on an electronics side of the substrate that is opposite the wound side of the dressing layer; a plurality of electrodes electrically coupled to the flexible printed circuit board; and a plurality of temperature sensors electrically coupled to the flexible printed circuit board, wherein at least one device of the plurality of devices differs from at least one other device of the plurality of devices in at least one of the following parameters: spacing between electrodes; spacing between temperature sensors; length or width of the dressing layer; electrical stimulation parameters; length or width of the temperature sensors; or length or width of the electrodes.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A device comprising:
a multi-layered, flexible substrate having
a dressing layer positioned on a wound side of the substrate, and
a flexible printed circuit board layer positioned on an electronics side of the substrate that is opposite the wound side of the dressing layer;
a plurality of electrodes electrically coupled to the flexible printed circuit board;
a plurality of temperature sensors electrically coupled to the flexible printed circuit board; and
a controller in electrical communication with the plurality of electrodes and the plurality of temperature sensors, wherein the controller is configured to:
control an electrical current between at least two electrodes of the plurality of electrodes to provide a series of electrical stimulations to treat a wound, cause application of a voltage across the wound during a time between sequential electrical stimulations of the series of electrical stimulations, receive signals from the at least two electrodes in response to application of the voltage, determine, based on the received signals from the at least two electrodes, an impedance between the at least two electrodes, and receive a signal from each temperature sensor of the plurality of temperature sensors.

2. The device of claim 1, wherein the dressing layer defines a plurality of openings, wherein the plurality of electrodes are received within corresponding openings of the plurality of openings in the dressing layer, and wherein the plurality of temperature sensors are received within corresponding openings of the plurality of openings in the dressing layer.

3. The device of claim 1, wherein the device has a longitudinal axis wherein a first temperature sensor of the plurality of temperature sensors is configured for positioning within an area of a wound and a second temperature sensor is spaced from the first temperature sensor along the longitudinal axis of the device.

4. The device of claim 3, wherein the plurality of electrodes comprises a first electrode and a second electrode, wherein the first and second electrodes and the first and second temperature sensors are aligned along the longitudinal axis, wherein the first temperature sensor is positioned in a space between the first and second electrodes, and wherein the second temperature sensor is positioned outside of the space between the first and second electrodes.

5. The device of claim 4, wherein the first temperature sensor is spaced from the second temperature sensor by at least four centimeters.

6. The device of claim 3, wherein each electrode of the plurality of electrodes is elongate along a transverse axis that is perpendicular to the longitudinal axis.

7. The device of claim 1, wherein the plurality of electrodes are flexible doped PDMS electrodes.

8. The device of claim 1, wherein the dressing layer is at least partially transparent.

9. The device of claim 8, wherein at least a portion of the flexible printed circuit board layer is transparent, and wherein the flexible printed circuit board layer further comprises an occlusive layer that surrounds the at least a portion of the flexible printed circuit board that is transparent.

10. The device of claim 1, wherein the flexible printed circuit board layer comprises an LCP layer comprising photolithographic patterning that defines copper traces.

11. The device of claim 10, wherein the printed circuit board further comprises laser machined via trenches that are electroplated with copper to define vias that extend between the copper traces and respective electrodes of the plurality of electrodes.

12. The device of claim 11, wherein the plurality of electrodes are photolithographically fabricated on the wound side of the printed circuit board.

13. The device of claim 12, wherein the temperature sensors comprise platinum and are photolithographically fabricated on the wound side of the printed circuit board.

14. The device of claim 1, wherein the plurality of temperature sensors are configured to exhibit a linear response within a range between 35° C. and 40° C.

15. The device of claim 1, wherein the controller is further operative to transmit, to a remote module, a signal corresponding to the signal from each temperature sensor.

16. The device of claim 1, wherein the printed circuit board defines an outer surface of the device.

17. The device of claim 1, wherein the controller comprises an impedance meter that is configured to apply the voltage across the wound.

18. The device of claim 1, wherein the controller is in communication with an impedance meter, and wherein the impedance meter is configured to apply the voltage across the wound.

19. A system comprising:
a device comprising
a multi-layered, flexible substrate having
a dressing layer positioned on a wound side of the substrate, and
a flexible printed circuit board layer positioned on an electronics side of the substrate that is opposite the wound side of the dressing layer,
a plurality of electrodes electrically coupled to the flexible printed circuit board,
a plurality of temperature sensors electrically coupled to the flexible printed circuit board, and
a controller in electrical communication with the plurality of electrodes and the plurality of temperature sensors, wherein the controller is configured to:
control an electrical current between at least two electrodes of the plurality of electrodes to provide a series of electrical stimulations to treat a wound,
cause application of a voltage across the wound during a time between sequential electrical stimulations of the series of electrical stimulations,
receive signals from the at least two electrodes in response to application of the voltage,
determine, based on the received signals from the at least two electrodes, an impedance between the at least two electrodes, and
receive a signal from each temperature sensor of the plurality of temperature sensors; and
a remote module in communication with the controller of the device.

* * * * *